United States Patent [19]

Hoagland

[11] Patent Number: 5,273,425
[45] Date of Patent: Dec. 28, 1993

[54] PORTABLE PET TEETH CLEANING ABRASIVE INSTRUMENT

[76] Inventor: Richard W. Hoagland, Lake Trail East, Morristown, N.J. 07960

[21] Appl. No.: 951,887

[22] Filed: Sep. 28, 1992

[51] Int. Cl.5 .................. A61D 5/00; B24D 15/00
[52] U.S. Cl. ........................................ 433/1; 51/392
[58] Field of Search ............... 433/1; 15/167.1, 167.2; 51/391, 392, 393

[56] References Cited

U.S. PATENT DOCUMENTS

| | | | |
|---|---|---|---|
| 323,305 | 7/1885 | Evans | 15/167.1 X |
| 1,427,503 | 8/1922 | Wake | 51/392 |
| 1,470,710 | 10/1923 | Davis | 15/167.1 |
| 1,801,915 | 4/1931 | Gray | 15/167.1 X |
| 1,918,521 | 7/1933 | Chott | 15/167.1 |
| 1,924,152 | 8/1933 | Coney et al. | 15/167.1 |
| 2,429,550 | 10/1947 | Hein | 51/392 X |
| 2,599,191 | 6/1952 | Meunner | 15/167.1 |
| 2,819,482 | 1/1958 | Applegate | 15/167.1 X |
| 2,877,483 | 3/1959 | Alvistur | 15/167.1 X |
| 2,915,767 | 12/1959 | Vaughan | 15/167.1 |
| 3,103,680 | 9/1963 | Krichmar | 15/167.1 |
| 3,337,893 | 8/1967 | Fine et al. | 15/167.1 X |
| 3,491,396 | 1/1970 | Eannarino et al. | 15/167.1 X |
| 3,613,143 | 10/1971 | Muhler et al. | 15/167.1 |
| 3,643,386 | 2/1972 | Grzyll | 51/391 |
| 3,956,858 | 5/1976 | Catlin et al. | 51/393 |
| 4,263,691 | 4/1981 | Pakarnseree | 15/167.1 X |
| 4,462,136 | 7/1984 | Nakao et al. | 15/167.1 |
| 4,543,679 | 10/1985 | Rosofsky et al. | 15/167.1 X |
| 4,576,190 | 3/1986 | Youssef | 132/89 |
| 4,628,564 | 12/1986 | Youssef | 15/167.1 |
| 5,040,260 | 8/1991 | Michaels | 15/167.1 |
| 5,044,041 | 9/1991 | Ljungberg | 15/210 R |

Primary Examiner—Gene Mancene
Assistant Examiner—Nicholas D. Lucchesi
Attorney, Agent, or Firm—William T. Hough

[57] ABSTRACT

A portable instrument having an angular elongated handle with a free end and a distal end, with abrasive composition mounted on a lateral face of the distal end. The abrasive composition includes microscopic abrasive mineral embodied in phenolic resin encasing nylon fibrous strands mounted on a resilient synthetic sponge secured to the lateral face. The elongated handle closer to the distal end has an enlargement as a finger support. The distal end narrows to a thin thickness adapted to fit into narrow gaps adjacent a pet's teeth.

16 Claims, 2 Drawing Sheets

PORTABLE PET TEETH CLEANING ABRASIVE INSTRUMENT

This invention relates to a device or instrument for the cleaning of teeth of a pet.

PRIOR ART

While no relevant prior art was located in a patentability novelty search, patents of interest located are as follow, in a search in United States Patent & Trademark Office United States Class 15, subclass 167.1. None of the patents located related directly to use in the cleaning of teeth of pets, such as dogs or cats. U.S. Pat. No. 4,528,564 granted Dec. 16, 1986 to Youssef is directed to a device for directing liquid through bristles of a pointed end-mounted sponge having associated bristles, designated as being a toothbrush structure. U.S. Pat. No. 4,576,190 granted Mar. 18, 1986 to Yousseff likewise is directed to a non-abrasive sponge-mounted tooth-cleaning device. U.S. Pat. No. 5,044,041 to Ljungberg granted Sep. 3, 1991 is directed to a toothpick type device having oppositely spaced apart rows of serially-arranged consecutive teeth of thermoplastic. All other patents are directed to variations on toothbrushes, such as U.S. Pat. No. 3,337,893 granted on Aug. 29, 1967 to Fine et al. having opposite a bristles-side, an opposite face thereof carrying resilient sponge with woven fibers having twisted sharp cutting edges, and U.S. Pat. No. 323,305 issued Jul. 28, 1885 to Evans to a device called a toothbrush having surface of paraffin-soaked woven and rolled fabric, and U.S. Pat. No. 1,801,915 granted Apr. 21, 1931 to Gray directed to a handle mounting-structure for the mounting of a block of rubber thereon, and U.S. Pat. No. 1,599,191 granted Jun. 3, 1952 to Meunier directed to looped bristles, and U.S. Pat. No. 2,877,483 granted Mar. 17, 1959 directed to a mounted rubber sponge encased by plastic woven threads having interstices (holes) therebetween, and U.S. Pat. No. 1,470,710 granted Oct. 16, 1923 to Davis to a toothbrush having a plurality of abrasive penetrative straight stiff filaments within and enveloped by yielding fibrous vegetable or other cellulose, such that the filaments may be pushed through space to contact teeth during brushing. While no patent is known thereto, also there is a commercial finger-mountable tab of gauze (no apparent abrasive composition thereon) for use to clean a pet's teeth, having no disclosure as to its content and no mounting handle structure that would permits viewing and that would remove the risk of being bitten by the pet. The present inventor has heretofore made concerted but unsuccessful attempts to clean the teeth of a pet by use of a conventional nylon bristles toothbrush, including use therewith of dental dip and also with dentifrice.

BACKGROUND TO THE INVENTION

Typical commercially available toothbrushes have elongated handles with monofilament bristles mounted on a flattened laterally-facing face of a flattened toothbrush head at the distal end of the handle. The thin flexible typically nylon bristles are smooth monofilaments of which the ends of the bristles are cut-off at right angles to form the flat brush area. Cleansing of a person's teeth is accomplished by action of the sides and ends of the nylon bristles which move over the teeth. The person holding the handle of the toothbrush manipulates the angle and direction of the brush so as to access most of the tooth surface. A dentifrice, such as toothpaste is used for its foaming action so that loosened food particles can be more readily removed.

The above-described conventional toothbrush and the above-described mechanism thereof in attempted tooth cleaning, does not effectively remove stains and/or plaque. The bristles are ineffective in removing stains and/or semi-hardened plaque. With the present technology typically described above, a person must await a scheduled visit to the dentist or dental hygienist in order to have the plaque and stains removed by the use of metal scraping tools and/or electric cleaning device(s) in combination with typically a gritty paste.

The sole device (instrument) for attempted cleaning of the teeth of a dog, is the standard or conventional toothbrush, sometimes used in combination with special enzymatic dentifrice. As in cleaning human teeth with a toothbrush, this above-described approach with dogs, fails to remove established plaque and/or tartar from the dog's teeth, and prolonged and/or over zealous attempts to get at and attempts to remove the plaque and/or tartar from the dog's teeth, can cause pain and/or eventual exhaustion of patience of the dog or other pet, and/or irritability of the pet, perhaps associated with snapping and/or biting. Present approaches at cleaning a pet's teeth moreover is extremely slow and tedious and fails to do an effective or satisfactory job in removal of yellow stains that are so common on a dog's teeth, for example. Use of metal dental instruments in attempts to clean (for example) a dog's teeth, requires great care to avoid hurting or causing pain or injury to the tender tissue, or to cutting or tearing such tissue, even with the exercise of great care and patience. Moreover, the task is made more difficult normally arising from long or protracted periods between attempts to clean the teeth of a pet, allowing the teeth of the dog or cat, (for example) to accumulate yellow and brownish plaque and tartar, and for it to be hardened to a greater degree than typically on human teeth that receive a higher degree and more frequent care.

OBJECTS OF THE INVENTION

Accordingly, objects of the invention include the overcoming and/or avoiding of problems and difficulties above-described.

Another object is to obtain a novel portable device (instrument) utilizable to effectively and safely clean teeth of a pet devoid of hurting or injuring the pet, and/or devoid of irritating gum tissue of the pet, and/or devoid of hazardous risk of being bitten by the pet during a tooth-cleaning operation.

Another object is to obtain a novel portable device (instrument) by which a nonprofessional person (not a veterinarian or the like) may easily see and reach areas in need of cleaning devoid of blocking view with the hand(s), and/or making possible the concurrent use of tender loving care with accompanying continued confidence and patience of the pet dog or cat, typically.

Another object is to obtain a novel portable device making use of an improved combination of elements of improved effectiveness in removing tartar and/or plaque and/or stains from the surfaces of teeth of a pet such as a dog and/or cat.

Another object is to obtain a novel portable device having a shape of its working or cleaning end portion, shaped and/or structured to better enable reaching into and cleaning spaces between and/or beside teeth of a pet, which access heretofore has not been easily nor readily available devoid of above-discussed problems and difficulties.

Other objects become apparent from the preceding and following disclosure.

SUMMARY OF THE INVENTION

The invention broadly may be defined as a portable handle-mounted pet teeth-cleaning device, having elements in combination as follow. A handle structure and mechanism thereof is for grasping and maneuvering a teeth surface cleaning structure(s) and mechanism thereof when mounted thereon. The handle structure and mechanism thereof include an elongated member having a proximal free end and a distal end having the cleaning structure(s) and mechanism thereof mounted thereof. Tooth surface cleaning structure(s) and mechanism thereof abrade away residual coating debris from tooth of at least one tooth of a pet. The tooth surface cleaning structure(s) and mechanism thereof include at least one elongated face substantially laterally facing and having mounted therealong first abrasive structure adapted to abrade the residual coating debris. The handle structure and mechanism thereof is mounted on the distal end.

In a first preferred embodiment, as an improvement on the above-described broad invention on the portable handle-mounted pet teeth-cleaning device, the first abrasive structure comprises a nontoxic resinous composition.

In a second preferred embodiment, as an improvement on the above-described first preferred embodiment, the first abrasive structure includes a plurality of strands of synthetic fiber coated by the nontoxic resinous composition.

In a third preferred embodiment, as an improvement on the above-described second preferred embodiment, the resinous composition includes at least one of predominantly a phenolic resin and an acrylic resin.

In a fourth preferred embodiment, as an improvement on the above-described third preferred embodiment, the first abrasive structure includes first mineral particles supported by the resinous composition on at least the plurality of synthetic fibrous strands.

In a fifth preferred embodiment, as an improvement on the above-described fourth preferred embodiment, the mineral particles are microscopic in size.

In a sixth preferred embodiment, as an improvement on the above-described fifth preferred embodiment, the synthetic fibrous strands includes predominantly at least one of nylon strands and polyester strands.

In a seventh preferred embodiment, as an improvement on the above-described sixth preferred embodiment, the elongated member has an enlarged portion spaced away from a distal end closer to the distal end as compared to a free end. The enlarged portion is of a size and shape adapted to facilitate handling and directing movement of the elongated portion when moving the first abrasive structure against residual coating debris coated on a pet's tooth surfaces.

In an eighth preferred embodiment, as an improvement on the above-described seventh there is included a resilient composition at least partially supporting the nontoxic resinous composition on the elongated face.

In a ninth preferred embodiment, as an improvement on the above-described eighth preferred embodiment, the resilient composition comprises plastic foam.

In a tenth preferred embodiment, as an improvement on the above-described ninth preferred embodiment, there is included an opposite elongated face facing an opposite lateral direction from the lateral direction of the first face. A second abrasive composition of has a second abrasive structure of particle size larger than the first abrasive structure. The second abrasive structure is mounted on the opposite elongated face.

In an eleventh preferred embodiment, as an improvement on the above-described tenth preferred embodiment, the elongated member includes a bend thereof of a minor angle sufficient to facilitate directing the distal end laterally into a mouth of a pet when cleaning a pet's teeth.

In a twelfth preferred embodiment, as an improvement on the above-described first embodiment, there is the same improvement as set forth in the third preferred embodiment.

In a thirteenth preferred embodiment, the first abrasive structure includes first mineral particles supported by the resinous composition, as an improvement on the above-described first embodiment.

In a fourteenth preferred embodiment, there is the same improvement as set forth in the fifth preferred embodiment, as an improvement on the above-described thirteenth preferred embodiment.

In a fifteenth preferred embodiment, the abrasive structure includes a plurality of predominantly nylon strands, as an improvement on the above-described fifth preferred embodiment.

In a sixteenth preferred embodiment, there is the same improvement as set-forth in the seventh preferred embodiment as an improvement on the above-described first embodiment.

In a seventeenth preferred embodiment, there is included a resilient composition at least partially supporting the nontoxic resinous composition on the elongated member along a length of the distal end, as an improvement on the above-described first embodiment.

In an eighteenth preferred embodiment, there is the same improvement as set-forth in the ninth preferred embodiment, as an improvement on the above-described seventeenth preferred embodiment.

In a nineteenth preferred embodiment, there is included a first elongated face along a length of the elongated member and facing a first lateral direction and supporting the first abrasive structure. Also there is included an opposite second elongated face facing an opposite lateral direction from the first lateral direction. A second abrasive composition has a second abrasive structure of particle size larger than the first abrasive structure. The second abrasive structure being mounted on the opposite elongated face, as an improvement on the above-described broad invention.

In a twentieth preferred embodiment, there is the same improvement as set forth in the eleventh preferred embodiment, as an improvement on the above-described first embodiment.

In a twenty-first preferred embodiment, as an improvement on the above-described first embodiment, the elongated member narrows to a predetermined narrow thickness at the distal end such that narrowed distal end structure is maneuverable within space adjacent a pet's teeth.

The invention may be better understood by making reference to the following figures.

THE FIGURES

FIG. 1 diagrammatically illustrates a top and end perspective view of a preferred embodiment of the invention.

FIG. 2 diagrammatically illustrates the same embodiment as that of FIG. 1, except in side in-part view, showing a length of the elongated handle member.

FIG. 3 diagrammatically illustrates the same embodiment as that of FIGS. 1 and 2, except in distal end view of the head structure of the distal end.

FIG. 4 diagrammatically illustrates an alternate preferred embodiment of the invention, in side view thereof, showing a length of the elongated handle member and illustrating the diminishing thickness of the distal end of the elongated handle member as a part of the head structure, otherwise except for having abrasive on solely one face thereof, corresponding otherwise to the FIG. 1 embodiment as shown in perspective view.

FIG. 5 diagrammatically illustrates the same embodiment as that of FIG. 4, except being an elevated plan end view of the distal end 6A and of the abrasive structure thereof.

DETAILED DESCRIPTION

The present invention, above-described in its various embodiments, is not meant to be a substitute for the typical conventional nylon toothbrush, for example. Instead, the device of the present invention is meant to be used as a supplement to a conventional tooth brush, more particularly the present invention being directed to the removal of stains, and/or plaque and/or tarter from the teeth of pets such as typically cats and/or dogs, i.e. to perform functions heretofore not readily nor adequately performed by the conventional nor prior art toothbrushes.

The inventive device as illustrated is typically a plastic handled device similar to that of a standard toothbrush. Instead of bristles, however, the cleaning device has a pad typically approximately about $\frac{3}{8}$ inch wide and from about $\frac{3}{4}$ inch to about one and $\frac{1}{4}$th inch long by about $\frac{1}{8}$th inch high. Size is not critical except to the extent that larger sizes can be used for larger animals, while small sizes would be required for small pets, and except that normally a reasonably smaller size (large enough to grasp and handle adequately) is more adept for use in getting into confined spaces and around various teeth and tooth surfaces. The pad is typically composed of fine preferably nylon or polyester fibers (but not necessarily limited thereto), and typically is impregnated with very fine and/or microscopic abrasive mineral particles as aforestated. Acrylic or phenolic resins hold the thin fibers together to form typically a pad and at the same time hold the tiny abrasive particles in place along each fiber or fibrous strand. A manufactured tradename of this abrasive pad material is SCOTCH-BRITE (trademark) having presently catalogue number 445 as manufactured by the 3M Company. Another typical product suitable for the present invention is the white fibrous scrubbing surface that is found on the sponge scrubber O-CEL-O (trademark) as manufactured by General Mills, Inc.. The coated abrasive fiber pads may be of various degrees of abrasiveness. The typical pad is connected to the plastic handle by any conventional and/or suitable way and/or mechanism, but normally by using a cyanoacrylate glue or other satisfactory glue. In the two-sided embodiment such as typically illustrated in FIGS. 1 through 3, the second pad is composed of a plastic cellular sponge of approximately $\frac{1}{8}$th inch thick, and a liquid applied typically acrylic abrasive coating and/or as is presently found in a product named SCROUNGE (trademark) that is manufactured by GUARDSMAN (trademark). This second pad is also attached to the plastic handle using a cyanoacrylate glue or any other satisfactory glue and/or conventional or other equivalent mechanism or composition.

Figure 1:
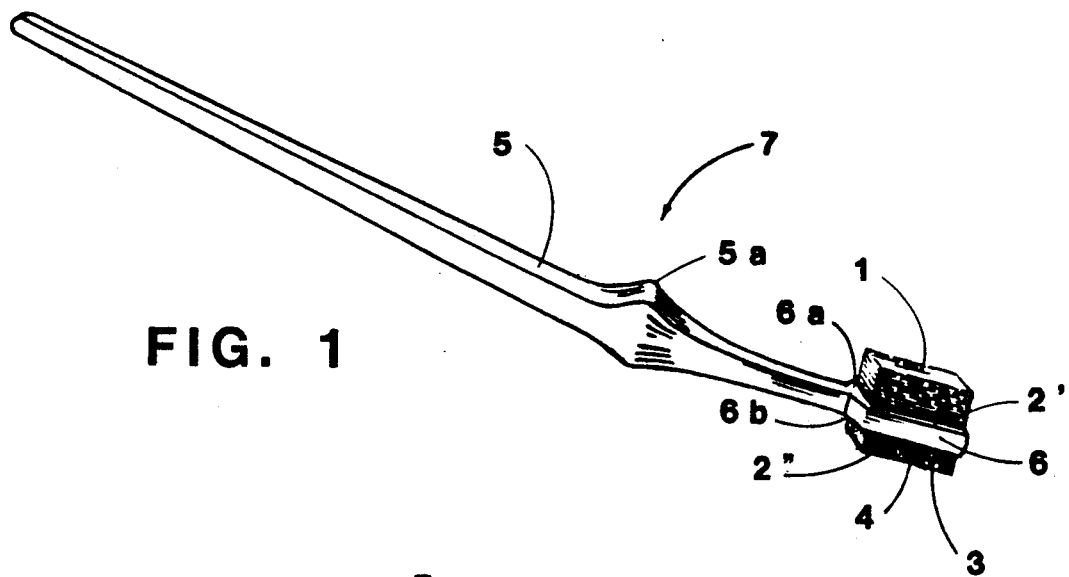
Figure 2:
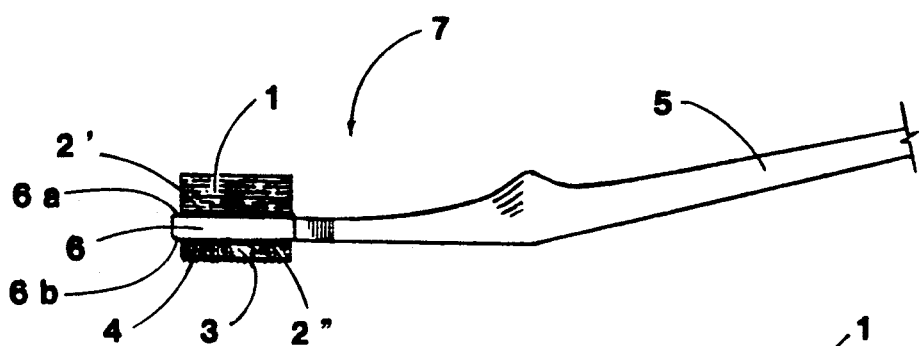
Figure 3:
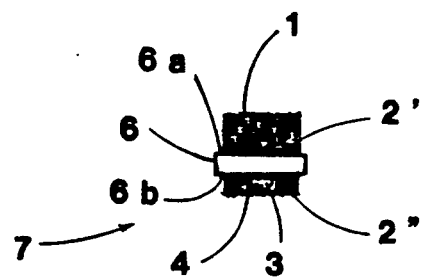

It is not only not intended that the present device always necessarily be used alone devoid of complementing dentifrice, but the combination use of dentifrice with the abrasive scrubbing head-surface(s) of the present invention is most desirable for optimal and/or most effective cleaning. However, use of such dentifrice or the like, is not required nor essential nor critical to the beneficial use of the present inventive device. The second and additional abrasive surface and combination of the invention as illustrated on the opposite face, for FIGS. 1 through 3, is intended to be used and normally required—utilizing larger abrasive particles—to effectively clean away plaque that is of the hardest variety; however, normally, the embodiment embodying the microscopic sized abrasive mineral particles is more than adequate.

Also, another manufacturer of abrasive pads—of which the present invention is adapted to utilize the same type and/or identical pad material for the present inventive combination as above-described and claimed hereinafter, is the company Reckitt & Coleman, Inc. that produces "CHORE-BOY" (trademark) of which the white abrasive pad is mounted on a sponge, of which that pad is utilizable for the present invention.

A typical conventional glue suitable for use for gluing as previously noted, is cyanoacrylic glue known as "SUPER GLUE" (trademark), or any other satisfactory glue. A typical resilient material or sponge is plastic cellular foam sponge of commercially available conventional type. Liquid applied acrylic abrasive coating is conventionally commercially available, typically as for example found in a product above-noted, named "SCROUNGE" (trademark) manufactured by Guardsman Products, Inc.—apparently covered by U.S. Pat. No. 4,264,337.

While preferred abrasive composition non-toxic resins have been above specified as preferred embodiments of the invention, the invention clearly is not limited thereto, any non-toxic water-insoluble resin which in its original or conventionally modified states is suitable for anchoring and embodying typically mineral (or other) abrasive particles, is suitable and is contemplated as within the scope of the present invention. Also, the hardness of the resin also may beneficially contribute to the successful removal of tartar, plaque and/or stains from the teeth of pets. Accordingly, it is noteworthy to recognize that resins fall into four basic groups—as listed in LANGE'S HANDBOOK OF CHEMISTRY, Twelfth Edition (and also in subsequent editions as further supplemented) found on pages 7–436 through 7–445, all within the contemplation and application as a part of the present invention, namely: a) natural gum resins of vegetable origin which contain some resinous constituents in admixture with carbohydrate bodies, so that the resulting complex will yield some water-soluble constituents; b) natural resins of animal origin; and c) new resin (same as natural gum resins, but with the solvents gone completely) and d) natural hydrocarbon resins. Typical of these resins are—gum accroides which typically heretofore have been used to color spirit varnishes and nitrocellulose liquors and in sealing wax, typically derived from a species of yellow or red Xanthorroea in Australia, and also Gum benzoin (composed of 69% cinnamic acid esters, 30% cinnamic acid and 1% or less of vanillin taken from Sumatra and Siam Styrax Benzoin, and Cameron Copal from West Africa, and Canadian Balsam—used in optometric work, from abies balsamea, and many others such as Columbia Copal, Congo Copal, Copaiba Baisam, Dammar, Demerara Copal, Dragon's Blood, East India, Gakbabynm Gamboge, Gilsonite, Gurjun Balsam, Jalap (resin of), Kaaraya gum (India Gum), etc., as typically set-forth in the Physical and Chemical Properties Natural Resin-list of Organic Chemistry handbook.

Natural resins are typically vegetable-derived and are typically amorphous mixtures of carboxylic acids, essential oils and terpenes occurring as exudations on the bark of many varieties of trees and/or shrubs. They are T typically combustible, electrically nonconductive, hard and glassy with conchoidal fracture(s) when cold, and soft and sticky below the glass transformation point. Most are soluble in alcohol, ethers and carbon disulfide, and insoluble in water. The best known of these are rosin and balsam, obtained from coniferous trees; these have a high acid content. Of more remote origin are such resins as kauri, congo, dammar, mastic, sandarac, and copal. Their typical use is in varnishes, adhesives and printing inks, as well as in synthetic products. Miscellaneous types of natural resins include shellac, obtained from the secretion of an Indian insect, typically used as a transparent coating; also there is amber which is a hard, polymerized resin that occurs as a fossil. Ester gum is a modified resin.

Acrylic fiber is a generic name for a manufactured fiber that is conventional and well known, in which the fiber-forming substance is any long-chain synthetic polymer composed of at least 85% by weight of acrylonitrile units (by definition of the Federal Trade Commission), having typically a tensile strength of 2 to 3 g/denier, and water absorption of 1.5 to 2.5% with typically a specific gravity of about 1.17. Acrylic resin is a composition of thermoplastic polymers and/or copolymers of acrylic acid, methacrylic acid, esters of these acids, or acrylonitrile. The monomers are colorless liquids that polymerize readily in the presence of light, heat, or catalyst such as benzoyl peroxide. Acrylic resins vary from hard, brittle solids to fibrous, elastomeric structures to viscous liquids, depending on the monomer used and the method of conventional polymerization. The production of acrylic fibers is conventional well known technology within the public domain.

As set forth in *Hackh's Chemical Dictionary*, Fourth Edition (and subsequent edition with supplemental description) at page 534, polyester is any polymer having structural units linked by ester groupings, obtained by conventional or other condensation of carboxylic acids with polyhydric alcohols. The polyester resin may be any of a group of synthetic resins which are polycondensation products of dicarboxylic acids with dihydroxy alcohols and are a special type of alkyd resin, but unlike other types, are not usually modified with fatty acids or drying oils. An outstanding characteric of these resins in their ability, when catalyzed, to cure or harden at room temperature under little or no pressure. Most polyesters now conventionally produced contain ethylenic unsaturation, generally introduced by unsaturated acids. The unsaturated polyesters are usually crosslinked through their double bonds with a compatible monomer, also containing ethylenic unsaturation, and thus becoming thermosetting. The principal unsaturated acids used are maleic and fumaric. Saturated acids, usually phthalic and adipic, may also be included. The function of these acids is to reduce the amount of unsaturation in the final resin, making it tougher and more flexible. The acid anydrides are often used if and when deemed desirable, and if conveniently available and/or applicable. The dihydroxy alcohols most generally used are ethylene, propylene, diethylene, and dipropylene glycols. Styrene and diallyphthalate are the most common cross-linking agents. Polyesters are resistant to corrosion, chemicals, solvents, etc, and are typically available as fibers, films, sheets, power and chips, for example. A polyester fiber is a generic name for a manufactured fiber (either as staple or continuous filament) in which the fiber-forming substance is any long chain synthetic polymer composed of at least 85% by weight of an ester of a dihydric alcohol and terephthalic acid (Federal Trade Commission). A typical one thereof is the Du Pont de Nemours Co. fiber designated DACRON (trademark) which is polyethylene terephthalate having typically a strength (staple) of 2.2 to 4.0 g. per denier, normally continuous filament having strength up to about 9.5 g per denier, with a melting point of about 264 degrees Centigrade, a water absorption of about 0.5%, and is nonflammable. Polyester resin is used in production of polyester fibers as conventional well known technology within the public domain.

In the following detailed description of the above-described Figures, common indicia are utilized for the same elements of different figures of the same embodiment, and related indicia are utilized for different embodiment(s) of other figures for elements of corresponding shape and/or function, to improve ease of understanding and following the invention. Once an element has been described, description is not repeated for other figures nor embodiment(s).

FIGS. 1, 2 and 3 illustrate a common embodiment.

FIG. 1 diagrammatically illustrates a top and end perspective view of a preferred embodiment 7 of the invention, there is illustrated the first abrasive structure 1 containing typically the microscopic mineral abrasive embodied within resin anchored on Nylon (trademark) fibrous strands in pad form, adhered by adhesive layer 2' to the distal end flat-face 6a. The opposite flat face 6b has the second abrasive structure 4 inclusive of large-sized abrasive mineral particles embodied within resin anchored on cellular spong 3 in pad form, with the second abrasive structure being adhered by adhesive layer 2". Also shown is elongated member composed of the handle 5 as the proximal end 6 of the elongated member, and the intermediate enlargement 5a.

FIG. 2 diagrammatically illustrates the same embodiment as that of FIG. 1, except in side in-part view, showing a length of the elongated handle member 7. All FIG. 2 illustrated elements are described for FIG. 1.

FIG. 3 diagrammatically illustrates the same embodiment as that of FIGS. 1 and 2, except in distal end view of the head structure of the distal end. All FIG. 3 illustrated elements are described for FIG. 1.

Figure 4:
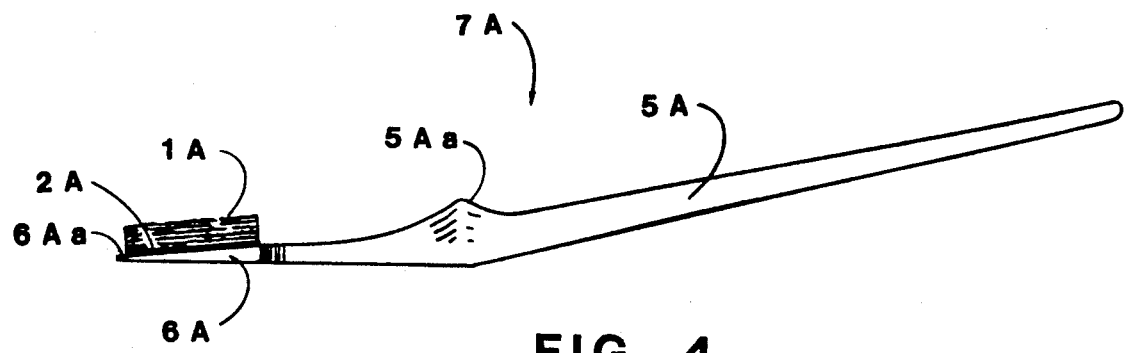
Figure 5:
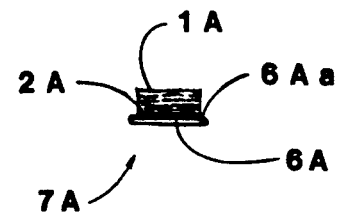

FIGS. 4 and 5 illustrate an alternate embodiment.

FIG. 4 diagrammatically illustrates an alternate preferred embodiment 7A of the invention, in side view thereof, showing a length of the elongated handle member composed of the handle 5A and enlarged portion 5Aa and illustrating the diminishing thickness of the distal end 6A of the elongated handle member as a part of the head structure, otherwise except for having abrasive on solely one face thereof, being corresponding otherwise to the FIG. 1 embodiment as shown in perspective view. Upper surface related indicia 6Aa corresponds to the embodiment of FIGS. 1 through 3 upper surface 6a, and likewise related indicia 1A corresponds to FIG. 1 indicia 1, and related indicia 2A corresponds to FIG. 1 indicia 2'.

FIG. 5 illustrates the same embodiment as FIG. 4, as an elevation plan end view of the distal end 6A and the abrasive structure 1A. The FIGS. 4 and 5 indicia identify different views of a common embodiment, the indicia thereof corresponding to the related indicia of the different embodiment of FIGS. 1 through 3. Accordingly, the indicia 1, 2', 5, 5a and 6a of FIG. 1 identify the same elements as indicia 1A, 2A, 5A, 5Aa and 6Aa of FIGS. 4 and 5.

The invention includes variations and modifications and substitution of equivalents within the skill of the ordinary artisan.

I claim:

1. A portable pet tooth cleaning device comprising in combination:
   a) a handle means including an elongated member having a proximal free end and a distal end;
   b) a tooth surface cleaning means having a size and shape to fit in the mouth of a pet, adapted to abrade away residual coating debris from the surface of at least one tooth of said pet, mounted at said distal end, comprising a first elongated face substantially facing in a first lateral direction and having mounted therealong a first abrasive structure adapted to abrade said debris from said surface, said abrasive structure consisting essentially of a plurality of synthetic fiber strands coated by a nontoxic resinous composition with a plurality of first mineral particles embedded therein.

2. The portable pet tooth cleaning device of claim 1, wherein said resinous composition includes predominantly at least one of a phenolic resin and an acrylic resin.

3. The portable pet tooth cleaning device of claim 2, wherein said mineral particles are microscopic in size.

4. The portable pet tooth cleaning device of claim 3, wherein said synthetic fiber strands include predominantly at least one of nylon strands and polyester strands.

5. The portable pet tooth cleaning device of claim 4, wherein said elongated member has an enlarged portion of increased width adjacent to said distal end, of a size and shape to facilitate handling and directing movement of the elongated member when moving said first abrasive structure against residual coating debris on a pet's tooth surface.

6. The portable pet tooth cleaning device of claim 5, further including a second elongated face, facing an opposite lateral direction from said first elongated face and having mounted thereon a second abrasive structure including second mineral particles of particle size larger than said first mineral particles, embedded therein.

7. The portable pet tooth cleaning device of claim 6, further including a resilient composition at least partially supporting said second abrasive structure on said second elongated face.

8. The portable pet tooth cleaning device of claim 7, wherein said resilient composition comprises plastic foam.

9. The portable pet tooth cleaning device of claim 8, wherein said elongated member includes an angular bend sufficient to facilitate directing said distal end into a mouth of a pet.

10. The portable pet tooth cleaning device of claim 3, wherein said plurality of synthetic fiber strands are predominantly nylon strands.

11. The portable pet tooth cleaning device of claim 3, wherein said elongated member has an enlarged portion of increased width adjacent to said distal end, of a size and shape to facilitate handling and directing movement of the elongated member when moving said first abrasive structure against residual coating debris on a pet's tooth surface.

12. The portable pet tooth cleaning device of claim 1, further including a second elongated face, facing an opposite lateral direction from said first elongated face and having mounted thereon a second abrasive structure including second mineral particles of particle size larger than said first mineral particles, embedded therein.

13. The portable pet tooth cleaning device of claim 12, further including a resilient composition at least partially supporting said second abrasive structure on said second elongated face.

14. The portable pet tooth cleaning device of claim 13, wherein said resilient composition comprises plastic foam.

15. The portable pet tooth cleaning device of claim 1, wherein said elongated member includes an angular bend sufficient to facilitate directing said distal end into the mouth of a pet.

16. The portable pet tooth cleaning device of claim 1, wherein said elongated member narrows to a predetermined thickness at said distal end such that said distal end is maneuverable within space adjacent a pet's teeth.

* * * * *